US009090881B2

(12) United States Patent
Harper et al.

(10) Patent No.: US 9,090,881 B2
(45) Date of Patent: Jul. 28, 2015

(54) METHOD FOR THE EFFICIENT AND CONTINUOUS GROWTH AND HARVESTING OF NUTRIENT-RICH PHYTOPLANKTON AND METHODS OF USING THE SAME

(75) Inventors: Margaret Harper, Nanaimo (CA); Arturo Ramirez, Nanaimo (CA)

(73) Assignee: Canadian Pacific Algae Inc., Nanaimo B.C. (CA)

( * ) Notice: Subject to any disclaimer, the term of this patent is extended or adjusted under 35 U.S.C. 154(b) by 226 days.

(21) Appl. No.: 12/603,239

(22) Filed: Oct. 21, 2009

(65) Prior Publication Data

US 2010/0189806 A1       Jul. 29, 2010

Related U.S. Application Data

(60) Provisional application No. 61/107,173, filed on Oct. 21, 2008.

(51) Int. Cl.

| | |
|---|---|
| *C12N 1/20* | (2006.01) |
| *C12N 1/12* | (2006.01) |
| *A23L 1/28* | (2006.01) |
| *A23L 1/302* | (2006.01) |
| *A23L 1/303* | (2006.01) |
| *A23L 1/304* | (2006.01) |
| *C12P 7/64* | (2006.01) |
| *C12P 39/00* | (2006.01) |

(52) U.S. Cl.
CPC ... *C12N 1/12* (2013.01); *A23L 1/28* (2013.01); *A23L 1/302* (2013.01); *A23L 1/303* (2013.01); *A23L 1/304* (2013.01); *C12P 7/6409* (2013.01); *C12P 7/6427* (2013.01); *C12P 7/6436* (2013.01); *C12P 7/6463* (2013.01); *C12P 7/6472* (2013.01); *C12P 39/00* (2013.01); *A23V 2002/00* (2013.01); *Y02E 50/30* (2013.01)

(58) Field of Classification Search
None
See application file for complete search history.

(56) References Cited

U.S. PATENT DOCUMENTS

| | | | |
|---|---|---|---|
| 3,403,471 A | | 10/1968 | Clement et al. |
| 3,439,449 A | | 4/1969 | Huff |
| 3,650,068 A | | 3/1972 | Meyer et al. |
| 3,951,805 A | * | 4/1976 | Dodd ............................ 210/193 |
| 4,005,546 A | | 2/1977 | Oswald |
| 4,023,734 A | | 5/1977 | Herve |
| 4,253,271 A | | 3/1981 | Raymond et al. |
| 4,417,415 A | | 11/1983 | Cysewski et al. |
| 4,581,233 A | | 4/1986 | Herve et al. |
| 4,824,673 A | | 4/1989 | Herve et al. |
| 4,897,266 A | | 1/1990 | Herve et al. |
| 5,081,036 A | | 1/1992 | Familletti |
| 5,547,997 A | | 8/1996 | Kludas |
| 6,346,252 B1 | | 2/2002 | Moigne |
| 6,540,808 B2 | | 4/2003 | Ma et al. |
| 2003/0143659 A1 | * | 7/2003 | Bijl et al. ........................ 435/67 |
| 2004/0168648 A1 | | 9/2004 | Ayers |

FOREIGN PATENT DOCUMENTS

| | | | |
|---|---|---|---|
| JP | 61192281 A | | 8/1986 |
| JP | 05308970 A | | 11/1993 |
| JP | 05308978 A | | 11/1993 |
| JP | 06098786 A | | 4/1994 |
| JP | 07075556 A | | 3/1995 |
| WO | PCT/CA2006/00399 | | 6/2006 |
| WO | WO2006/096986 | * | 9/2006 ............... C12N 1/12 |
| WO | PCT/IB2009/007382 | | 4/2010 |

OTHER PUBLICATIONS

Azarian et al., Iranian Journal of Public Health, vol. 36, No. 4, 2007, pp. 57-64.*
Jochem et al., Marine Biology (1999) vol. 135: pp. 721-728.*
Haug et al. "Polysaccharides of Marine Diatoms with Special Reference to Chaetoceros Species" Marine Biol. vol. 34 (1976) pp. 217-222.
Zhang et al. "Sustainable, High-Yielding Outdoor Mass Cultures of *Chaetoceros muelleri* var. subsalsum and *Isochrysis galbana* in Vertical Plate Receptors." Marine Biotech. vol. 5 (2003) pp. 302-310.
"Frond." The American Heritage® Dictionary of the English language, Fourth Edition. Houghton Mifflin Company, 2004. Retrieved Mar. 23, 2007. <Dictionary.com http://dictionary.reference .com/browse/frond>.
http://web.archive.org/web/*/http://www.truestarhealth.com/Notes/2836004.html. (Web Publication Date: Apr. 23, 2004). Date accessed: Mar. 23, 2007.
Sunlit Ocean (Euphotic) Zone Animal Printouts. Internet Archive Date: Aug. 31, 2004 [Retrieved from the Internet on: Mar. 21, 2008]. Retrieved from: http://web.archive.org/web/*/http://www.enchatedlearning.com/biomes/ocean/sunlit/.
"Thallus." The American Heritage® Science Dictionary. Retrieved Mar. 23, 2007, from Dictionary.com website: http://dictionary.reference.com/browse/thallus.
De Pauw et al., "Mass culture of microalgae in aquaculture systems: Progress and constraints", (1984) vol. 116-117, pp. 121-134.
Eriksen "The technology of microalgal culturing", *Biotechnol. Lett.*, (2008), vol. 30, No. 9, pp. 1525-1536.

(Continued)

*Primary Examiner* — Allison Fox
*Assistant Examiner* — Yvonne Pyla
(74) *Attorney, Agent, or Firm* — Dunlap Codding, P.C.

(57) ABSTRACT

Methods of growing and harvesting multiple species of phytoplankton are disclosed herein. The method generally includes four steps, namely: (1) collecting phytoplankton seawater containing multiple species of naturally-occurring phytoplankton directly from a source of seawater; (2) adding nutrients to the phytoplankton seawater to proliferate the multiple species of naturally-occurring phytoplankton to a predetermined density; (3) separating the multiple species of naturally-occurring phytoplankton from the phytoplankton seawater to form a phytoplankton concentrate; and (4) collecting the phytoplankton concentrate such that the collected phytoplankton of the phytoplankton concentrate remain in a substantially intact cellular state.

33 Claims, 1 Drawing Sheet

(56) References Cited

OTHER PUBLICATIONS

Gudin et al., "Cell Fragility-The Key Problem of Microalgae Mass Production in Closed Photobioreactors", *Bioresource Technology*, (1991) vol. 38, pp. 145-151.

Rausch, T. "The estimation of micro-algai protein content and its meaning to the evaluation of algai biomass I. Comparison of methods for extracting protein." Hydrobiologia, Mar. 1981, vol. 78, No. 3, pp. 237-251, ISSN: 0018-8158. See whole document.

Margaritis et al. "Novel bioreactor systems and their applications." Nat Biotechnol, May 1984, vol. 2, pp. 447-453, ISSN: 1087-1056. See p. 449.

Richmond et al. "Technological aspects of mass cultivation—a general outline" In: CRC Handbook of microalgae mass culture. Edited by A. Richmond, Boca Raton: CRC Press, Inc., 1986, pp. 245-265. See pp. 257-258.

Jochem F.J., "Dark survival strategies in marine phytoplankton assessed by cytometric measurement of metabolic activity with fluorescein diacetate", Marine Biology, vol. 135, pp. 721-728, 1999.

\* cited by examiner

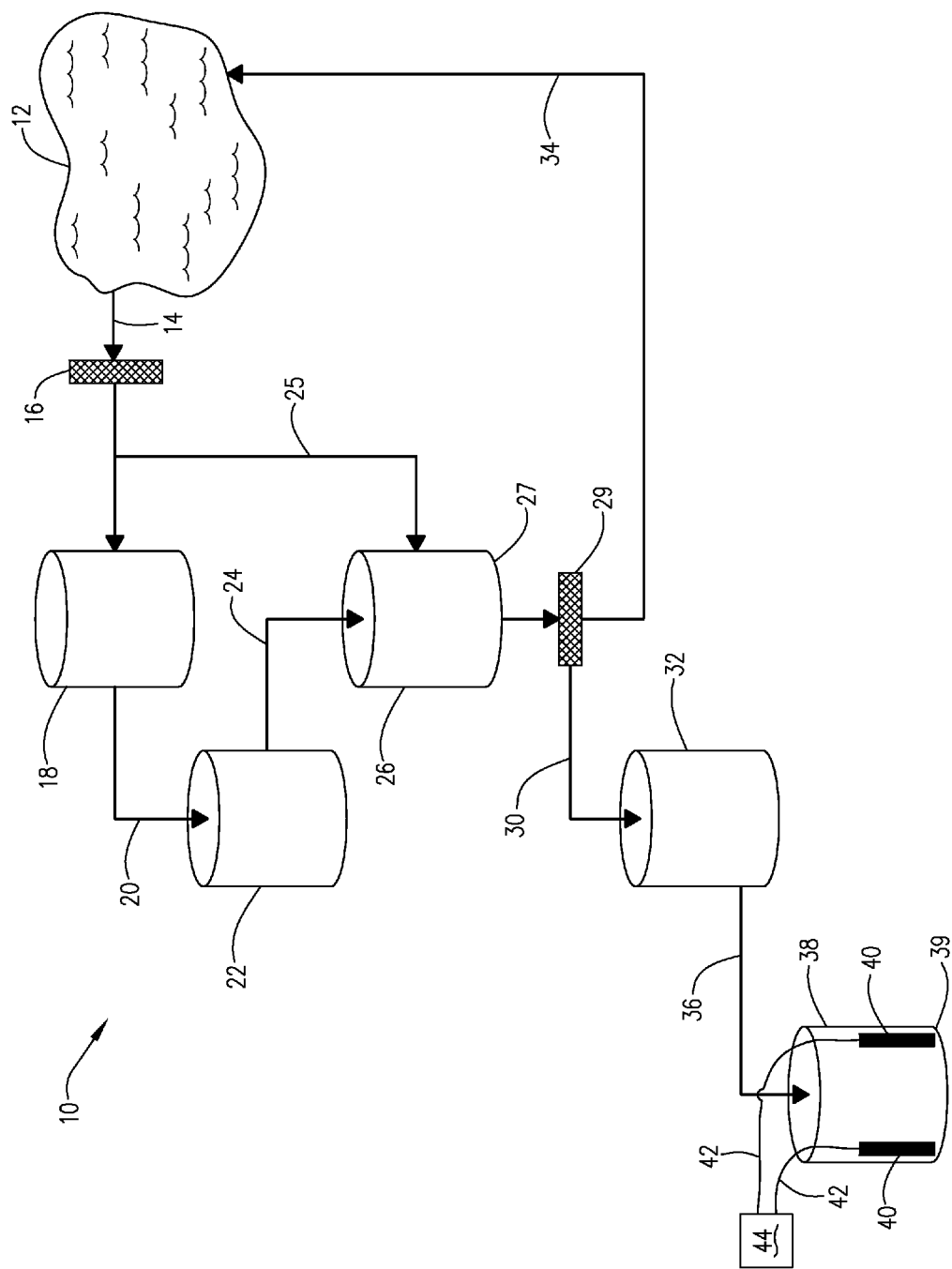

METHOD FOR THE EFFICIENT AND CONTINUOUS GROWTH AND HARVESTING OF NUTRIENT-RICH PHYTOPLANKTON AND METHODS OF USING THE SAME

CROSS-REFERENCE TO RELATED APPLICATIONS

This application claims benefit of U.S. Provisional Application No. 61/107,173, filed Oct. 21, 2008, which is hereby incorporated herein by reference in its entirety.

BACKGROUND OF THE INVENTION

Field of the Invention

The present invention relates to a method for collecting, continuously growing, and harvesting individual and polycultured species of phytoplankton for various applications, such as medicinal, nutriceutical, food processing, cosmetic, industrial, energy-related applications and the like. More particularly, the present invention relates to a method of harvesting Golden Brown Phytoplankton, in which the fatty acids and oils of the phytoplankton are substantially preserved in a whole and intact-state (i.e., not degraded by the current method), so as to provide improved products and additives for the use in the production of health-related products and bioenergy.

Brief Background of Spring Bloom Conditions and Phytoplankton

The phytoplankton (also known as microalgae) used in the presently disclosed process includes hundreds of species of photosynthetic, unicellular organisms belonging to the kingdom Protista. Phytoplanktons from a multitude of various taxonomic classes and orders flourish in temperate coastal waters, including, for example, the coastal waters bordering the province of British Columbia in Canada.

During the spring months, and especially during the late spring, phytoplankton proliferates at an accelerated rate in a process known as "spring bloom." When the temperature of the seawater is relatively cool, i.e., during the winter months, water is circulated from the bottom of the water column to the top of the water column, which pushes nutrients from the depths of the ocean into the euphotic region of the ocean. The euphotic region refers to the portion of the ocean (approximately the upper 20 meters of the ocean) that receives enough sunlight to allow photosynthesis to occur. In the early spring, the euphotic region has an ample abundance of nutrients to provide for phytoplankton growth; however, due to an insufficient amount of light to provide for continual photosynthetic proliferation and constant nutrient mixing by the environment, phytoplankton typically does not rapidly grow during this period.

As the water begins to warm in the late spring, the warm, oxygen and nutrient rich water remains in the euphotic region because warm water is less dense and has a tendency to rise to the top of the water column. This results in stratification of the water column, creating a top layer of warm, nutrient-rich water, known as the epilimnion, to be formed in the euphotic region. During the stratification period, the phytoplankton are maintained in the epilimnion layer of the euphotic region, and, as a result of the high concentration of nutrients and adequate sunlight conditions, the population of phytoplankton grows at an exponential rate. In most cases, the phytoplankton will consume many, if not all, of the nutrients in a matter of several weeks or months.

As previously mentioned, phytoplankton includes hundreds of species of unicellular, photosynthetic organisms belonging to the taxonomic kingdom Protista. Within this kingdom, there are various classes and orders of phytoplankton that can be utilized in the presently disclosed invention. Examples of these various classes and orders of phytoplankton include: (1) class Bacillariophyceae, and, particularly, the orders Centrales and Pennales; (2) class Dinophyceae, and, particularly, the orders of Prorocentrales, Dinophysiales, Gymnodiniales, Peridiniales, Noctilucales, and Pyrocystales; (3) class Raphidophyceae; (4) class Prymnesiophyceae; (5) class Dictyophyceae; (6) class Euglenophyceae; (7) class Prasinophyceae; (8) class Cryptophyceae; (9) class Chrysophyceae; and (10) class Chlorophyceae.

Accordingly, an object of the present invention is to provide a method that mimics the optimal "spring bloom" conditions so as to provide continual and exponential growth of phytoplankton year-round, rather than only during the late spring and early summer months.

Another object of the present invention is to provide a process by which the various classes and orders of phytoplankton are refined in such a way as to maintain the fatty acids and/or oils of the phytoplankton in a whole or intact state so as to provide a superior product for use in various industrial, medical, and biofuel applications. These and other objects, advantages, and features of the present invention will be apparent to those skilled in the art from a reading of the following detailed description of the present invention.

There are a number of distinct advantages associated with creating a phytoplankton product in which the phytoplankton's fatty acids and/or oils are kept substantially whole and intact. Some of these advantages include: (1) keeping the oils intact allow for the precise separation of fatty acids which are extremely valuable for use in various supplements, foods, and biosynthetic greases and fuels; (2) keeping the oils intact by not rupturing the phytoplankton cells create a superior product for bio-energy as approximately 100% of the oils are present; and (3) less additives are used to create the refined phytoplankton product (i.e., there is no need for a lysing or rupturing agent, such as sodium hydroxide).

BRIEF DESCRIPTION OF THE DRAWINGS

FIG. 1 is a schematic diagram illustrating a process for producing a refined phytoplankton product in accordance with the present invention.

DETAILED DESCRIPTION OF THE INVENTION

As broadly shown in FIG. 1, the present invention relates to a process 10 for producing a refined phytoplankton product, which includes the steps of collecting, growing, harvesting, and settling so as to produce a refined phytoplankton product. The refined phytoplankton product produced in accordance with the present invention includes at least one phytoplankton product in which the constituent fatty acids and/or oils of the product are maintained in a substantially intact state, as opposed to being degraded into less functional or effective fragments.

The initial step in the process 10 encompasses collecting an effective amount of phytoplankton-containing seawater from an existing source of seawater 12 via a seawater intake system 14, wherein the phytoplankton are naturally occurring (i.e., not seeded or inoculated) within the phytoplankton-containing seawater. The existing source of seawater 12 is preferably an ocean, but it should be understood that the source of seawater 12 is not limited to an ocean and may be any body of water sufficient to supply an effective amount of phytoplankton-rich seawater. In addition, it should be readily understood by a person having ordinary skill in the art that, while primarily described herein "seawater," the method could be adapted to collect and harvest phytoplankton from sources of water that vary in salinity concentration, including, but not limited to, freshwater species of phytoplankton. Similarly, while primarily described herein as utilizing multiple tanks, it should be understood that the currently disclosed and claimed method can be accomplished in a single tank or similar structure.

The seawater containing phytoplankton (hereinafter referred to as "seawater") is desirably passed through a filtering system 16 that prohibits larger pieces of algae (hereinafter referred to as "macroalgae") and organic materials larger than approximately four millimeters from entering the seawater intake system 14. It should be understood, however, that the filtering system may be altered so to accommodate larger or smaller sizes and amounts of macroalgae and other naturally occurring flora depending on the desired composition of the phytoplankton seawater and the seasonal changes associated with the source of seawater. Once the seawater has been collected by the seawater intake system 14, the seawater is stored in a storage facility 18, such as one or more temporary storage tanks. The seawater preferably remains in the storage facility 18 for a period of time of approximately 48 hours. However, it should be understood that the period of time that the seawater remains in the storage facility 18 may be adjusted to accommodate various growing requirements and conditions.

While in the storage facility 18, the seawater remains substantially deprived of external light and is aerated, such as with oxygen ($O_2$) gas, via a roots-type blower (not shown) so that the gas is diffused throughout the seawater by air stones (not shown) thereby preventing the phytoplankton in the seawater from entering an anaerobic state. Roots-type blowers and air stones are well known in the art and no further discussion of these devices is believed to be warranted. In addition, depriving the phytoplankton of light significantly accelerates the growth rate of the phytoplankton, reducing the growth cycle from approximately 8-10 days down to approximately 4-6 days (an increase in growth times of ~40%).

After the seawater has remained in the storage facility 18 for a predetermined period of time (e.g., approximately 48 hours), the seawater is transferred from the storage facility 18 via a conduit 20 into one or more starter tanks 22 where an effective amount of various nutrients are added to promote the rapid proliferation of the phytoplankton. Examples of nutrients which are used to promote the rapid proliferation of the phytoplankton include single compounds or combinations of: (1) phosphorous; (2) soluble potash; (3) boron; (4) chelated copper; (5) chelated iron; (6) chelated manganese; (7) molybdenum; (8) chelated zinc; (9) ethylemediamine; and (10) organic soluble fillers. Other compounds and combinations of compounds which are known in the art to be effective nutrients to stimulate the growth of phytoplankton can also be used, including, but not limited to, fish, human, and animal wastes. The phytoplankton can be optionally incubated within the starter tanks 22 for a predetermined period of time, for instance, up to seven days.

The starter tanks 22 can vary in volumetric size ranging from about 4 liters up to approximately 1,000,000 liters, with the size of the starter tanks 22 being selected for growing the phytoplankton in accordance with the season in which the phytoplankton is being grown. For instance, in the spring and summer, smaller starter tanks 22 are required to begin the growing process. Conversely, larger starter tanks 22 are required to initiate phytoplankton growth during the fall and winter months.

Following the addition of an effective amount of nutrients to the starter tanks 22 to stimulate phytoplankton growth, the seawater is again transferred via a conduit 24 to one or more grow-out tanks 26. Once within the grow-out tanks 26, the seawater is mixed with, for example, at least 750,000 liters of filtered and clean seawater that enters into the grow-out tanks directly from the source of seawater via conduit 25, which initiates the growth stage of the phytoplankton. It should be understood, however, that the volume of filtered and clean seawater can be any volumetric amount appropriate to achieve optimal or desired growth conditions of the phytoplankton. The grow-out tanks 26 are preferably constructed so as to have a depth dimension of at least 15 feet, and a more preferable depth of about 17 to about 18 feet.

The transfer of materials (e.g., phytoplankton and/or phytoplankton seawater) between the various tanks disclosed in the present invention can be facilitated in a number of different manners, such as through the use of one or more pumps (not shown), valves, through gravitational force or any other mechanism known in the art. For sake of simplicity, such mechanisms are not shown in the drawings, but are readily known to individuals skilled in the art as to their use of such mechanisms.

During the growing stage (and subsequent harvesting stage), individual or multiple monitoring measurements, namely seawater temperature, seawater turbidity, seawater pH, dissolved oxygen concentration within the seawater, seawater ammonia concentrations, seawater phosphate(s) concentrations, and weather conditions are taken periodically to monitor the progress and variable conditions of the growing stage. Depending on the information indicated by the monitoring measurement(s), additional nutrients can be added to the one or more grow-out tanks 26 as required to provide optimal growth conditions for the phytoplankton. The amount of nutrients added varies depending on the densities of the phytoplankton present within the grow-out tanks 26. For instance, a range of about 0 kilograms (if the phytoplankton density is low) to about 10 kilograms (if the phytoplankton density is high) per 1 million liters of seawater may be added to the grow-out tanks 26 to provide for optimal growth conditions. During the growing stage, and depending on the month of the growing stage, the grow-out tanks are desirably kept in a temperature range of about 12 to about 17 degrees Celsius in the summer months, and in a temperature range of about 6 to about 11 degrees Celsius during the winter months. It should be understood that the current method is not limited to these particular temperature ranges and can be accomplished in temperatures ranging from −10 to about 30 degrees Celsius. The monitoring period is desirably daily, however, the monitoring period can be any period of time effective to monitor the progress and variable conditions of the growing stage.

A unique aspect of the present method if that the phytoplankton are allowed to grow throughout 100% of the entire water column present in the grow-out tanks 26 using only natural sunlight (i.e., the phytoplankton is grows throughout the entire volume of seawater present in the about 17 to 18 feet tall grow-out tanks 26). This concept is unique and advantageous as it allows for the controlled and consistent growth of low-light phytoplankton species and also allows growth throughout the entire volume within the grow-out tanks 26 without having to expend the energy or financial costs associated with artificial light sources. It should be understood, however, that while described herein as using only natural light, the inventive concepts described herein may be implemented using one or more artificial light sources.

Once the phytoplankton cell densities reach a desired density, such as, for example, about 500,000 cells of phytoplankton per milliliter of seawater, the phytoplankton enters a second stage. The second stage of the process is referred to as a continuous harvesting stage. The continuous harvesting (and growing) of the phytoplankton is facilitated by withdrawing phytoplankton seawater from a bottom 27 of the grow-out tanks 26 and replacing the loss of water volume with clean and filtered seawater via conduit 25 with approximately equal amounts fresh seawater so as to maintain a relatively constant volume of seawater within the grow-out tanks 26.

The harvesting of the phytoplankton is accomplished by withdrawing the phytoplankton-rich seawater (hereinafter referred to as "phytoplankton water") from the bottom 27 of the grow-out tanks 26 via a conduit 28. The phytoplankton water withdrawn from the grow-out tanks 26 is passed through a filtering system 29, which acts to concentrate the phytoplankton water before being transferred via a conduit 30 into one or more distribution tanks 32. Any remaining clean, filtered seawater (i.e., any effluent passing through the filtering system 28) is recycled into the existing source of seawater 12, for instance, the ocean via an effluent conduit 34. The various conduits described herein are desirably constructed of four-inch PVC pipe, but it should be understood that the conduits can be constructed of any material, be of any shape, and be of any diameter as to facilitate the transfer of phytoplankton and/or phytoplankton water to and from the various tanks and/or to and from the existing water source 12.

The filtering system 28 desirably includes at least one filter (not shown) constructed of 20 micrometer mesh which is capable of trapping any cellular organic matter (for instance, phytoplankton cells) 20 micrometers or greater in size. It should be understood, however, that the filter system 28 can include multiple filters and that the size of the filter(s) can be of any size to stop the passing of cellular organic matter through the filter during the various stages of the presently disclosed process.

The filtering system 28, aside from removing any additional macroalgae and/or organic material, functions to concentrate the phytoplankton water entering the distribution tanks 32. After entering the distribution tanks 32, the phytoplankton water is transferred via a conduit 36 into one or more settling tanks 38 for further concentration of the phytoplankton water. Within the settling tanks 38, the phytoplankton water enters a third stage, namely the settling stage.

During the settling stage, the concentrated phytoplankton is allowed to settle in a bottom 39 of the settling tanks 38. 0.5% of citric acid by total volume of phytoplankton water is added to the settling tanks 38 to preserve the integrity of the phytoplankton, as well as accelerate the settling of the phytoplankton to the bottom 39 of the settling tanks 38. The addition of citric acid will settle and preserve the phytoplankton until the next processing step.

Alternatively, or in addition, after the phytoplankton water is passed through the filtering system 28 and transferred from the distribution tanks 32 into the settling tanks 38, the phytoplankton can be separated and concentrated via an electrical charge or an electrical coagulation process. The electrical coagulation process desirably includes placing one or more voltage plates 40 capable of conducting an electrical current within the settling tanks 38. The voltage plates 40 are desirably connected via one or more wires 42 to a voltage regulator 44, which transmits an electrical current to the voltage plates 40 thereby allowing separation of the phytoplankton from the phytoplankton water. This acts to concentrate the phytoplankton cells about the voltage plates 40. Once separation has occurred, the remaining seawater can be withdrawn from the settling tanks 38, leaving concentrated phytoplankton cells with relatively low moisture content.

The voltage plates 40 can be constructed of any material or combination (including both conductive and non-conductive materials) of materials and be of any shape that is capable of either conducting or facilitating the conduction of electrical current so as to effectuate the separation of phytoplankton cells. A particular voltage plate 40 material that has shown to be effective for creating separation of the phytoplankton is aluminum, but it should be understood that other materials of equal or greater efficacy may be used to achieve the separation in the presently disclosed invention.

While described herein primarily as filtering, electrical current, and gravitational settling separation, it should be understood that a number of methods can be used to separate the phytoplankton from the phytoplankton water, including, but not limited to, light, vibration, suction/siphoning, ultrasound, chemical addition/interaction, density differences, magnetism, and electromagnetism.

At the conclusion of the settling stage, the top, non-concentrated water is removed from the settling tanks 38, leaving settled, concentrated phytoplankton remaining at the bottom 39 of the settling tanks 38. At this point, the phytoplankton contains substantially intact fatty acids and/or oils (primarily due to the absence of lysing or rupturing the phytoplankton cells with a base agent) and the phytoplankton is placed in containers (not shown) for further processing and refining into a desired product, such as a liquid or powder product for use in various medicinal, nutriceutical, food processing, cosmetic, industrial, energy-related applications and the like. The concentrated phytoplankton may optionally be passed through another (or previously used) filtering system (not shown) which includes at least one filter as aforementioned so as to provide a desired consistency and water concentration of the concentrated phytoplankton. Whether the phytoplankton is either placed in containers or is optionally transferred through an additional filter system and then placed in containers, 1% ascorbic acid by total weight of phytoplankton is desirably added to the phytoplankton to preserve it until further processing.

Exemplary Compositional Analyses of
Phytoplankton Specimens

Compositional analyses of various specimens of harvested phytoplankton specimens produced in accordance with the process of the present invention are set forth in the following examples. However, it should be understood that the examples are illustrative only and are not to be construed as limiting the invention disclosed herein.

Example 1

A compositional analysis of an algae sample (Sample No. 54133-001) produced in accordance with the present invention is set forth.

Sample #: 54133-001
Sample Description: Algae Sample
Temp on Receipt: RT
Comment:

| Test | Compound | Specification Limit | Result | Detection Limit |
|---|---|---|---|---|
| Chlorophyll | | | 589.4 mg/100 g | |
| Fat - Acid Hydrolysis | | | 3.29% | 0.5% |
| Carotenoid Esters - total | | | 1.43% | |
| Total Polyphenols - UV | Total polyphenols | | 0.29% | n/a |
| Vitamin A - assay | Beta-carotene mcg divided by 6 | | 666 mcg/100 g | <10 IU/100 g |
| | Retinol | | ND mcg/100 g | |
| | Total vitamin A | | 666 mcg or RE/100 g | |
| Vitamin C - assay | | | ND mg/100 g | 50 ppm |
| Vitamin D assay | | | ND IU/100 g | |
| Vitamin E - profile | Alpha tocopherol | | ND mg/100 g | n/a |
| | Delta tocopherol | | ND mg/100 g | n/a |
| | Gamma tocopherol | | ND mg/100 g | n/a |
| Vitamin Test | B1 - Thiamine | | 2.4 mg/100 g | 0.1 mg/100 g |
| | B2 - Riboflavin | | 2.8 mg/100 g | 0.1 mg/100 g |
| | B3 - Niacin | | 14.6 mg/100 g | 0.1 mg/100 g |
| | B5 - Calcium D-Pantothenate | | 0.52 mg/100 g | 0.1 mg/100 g |
| | B6 - Pyridoxine HCl | | 2.2 mg/100 g | 0.1 mg/100 g |
| Fatty Acid Profile | | | see attached | |
| amino acid screen + tryptophan, cystine, methionine | alanine | | 1980 mg/100 g | 0.05% |
| | arginine | | 2130 mg/100 g | 0.05% |
| | aspartic acid | | 3590 mg/100 g | 0.05% |
| | cystine | | 360 mg/100 g | 0.05% |
| | glutamic acid | | 6210 mg/100 g | 0.05% |
| | glycine | | 1490 mg/100 g | 0.05% |
| | histidine | | 510 mg/100 g | 0.05% |
| | isoleucine | | 1200 mg/100 g | 0.05% |
| | leucine | | 1960 mg/100 g | 0.05% |
| | lysine | | 1630 mg/100 g | 0.05% |
| amino acid screen + tryptophan, cystine, methionine | methionine | | 470 mg/100 g | 0.05% |
| | phenylalanine | | 1270 mg/100 g | 0.05% |
| | proline | | 930 mg/100 g | 0.05% |
| | serine | | 1190 mg/100 g | 0.05% |
| | threonine | | 1150 mg/100 g | 0.05% |
| | tryptophan | | 410 mg/100 g | 0.05% |
| | tyrosine | | 880 mg/100 g | 0.05% |
| | valine | | 1400 mg/100 g | 0.05% |
| Amylase - alpha | | | <1 DU/g | |
| Lipase | | | 65 LU/g | |
| Proteolytic activity, bacterial source | | | 803.5 PC/g | |
| Vitamin B12 (bioassay) | | | 39.8 mcg/100 g | |
| Metal analysis by ICP/MS | Aluminum | | 190.30 ppm | |
| | Antimony | | 0.01 ppm | |
| | Arsenic | | 1.83 ppm | |
| | Barium | | 15.75 ppm | |
| | Beryllium | | <0.01 ppm | 0.01 ppm |
| | Bismuth | | <0.02 ppm | |
| | Boron | | 76.96 ppm | |
| | Cadmium | | 0.18 ppm | |
| | Calcium | | 6015.0 ppm | |
| | Chromium | | 6.40 ppm | |
| | Cobalt | | 0.15 ppm | |
| | Copper | | 39.70 ppm | |
| | Iron | | 1920.0 ppm | |
| | Lead | | 0.48 ppm | |
| | Lithium | | 2.04 ppm | |
| | Magnesium | | 1.467% | |
| | Manganese | | 892.0 ppm | |
| | Mercury | | 1.45 ppm | |
| Metal analysis by ICP/MS | Molybdenum | | 0.71 ppm | |
| | Nickel | | 1.85 ppm | |
| | Potassium | | 2.985% | |
| | Selenium | | 0.85 ppm | |
| | Silver | | <0.02 ppm | 0.02 ppm |
| | Sodium | | 10.37% | |
| | Strontium | | 186.90 ppm | |
| | Thallium | | <0.01 ppm | 0.01 ppm |
| | Thorium | | 0.06 ppm | |
| | Tin | | 0.59 ppm | |
| | Titanium | | 10.74 ppm | |

| Test | Compound | Specification Limit | Result | Detection Limit |
|---|---|---|---|---|
| | Uranium | | 0.37 ppm | |
| | Vanadium | | 1.01 ppm | |
| | Zinc | | 169.70 ppm | |
| | Zirconium | | 0.92 ppm | |

Methodology:
amino acid screen + tryptophan, cystine, methionine - protein bound amino acid by HPLC-UV detection
Amylase - alpha - FCC UV Spectraphotometry
Carotenoid Esters - total - UV Absorption
Chlorophyll - AOAC
Fat - Acid Hydrolysis - AOAC 950.54
Fatty Acid Profile - AOAC 996.06, AOCS Official Method Ce2-66
Lipase - FCC 4th edition (titration)
Metal analysis by ICP/MS - ICP/MS
Total Polyphenols - UV - Colorimeteric - using Folin-Ciocalteu reagent
Vitamin A - assay - AOAC Method of Analysis for Nutrition Labeling (1993) Chapter 36 modified
Vitamin B1, B2, B3, B5, B6 package - LC/MS/MS - in house
Vitamin B12 (bioassay) - USP 30 <171> modified for food
Vitamin C - assay - Extraction by AOAC Methods of Analysis for Nutrition Labeling (1993) Chapter 37, Analysis by HPLC
Vitamin D assay - AOAC Method of Analysis for Nutrition Labeling (1993) Chapter 38
Vitamin E - profile - HPLC Example 2

A compositional analysis of a freeze-dried Golden Brown Algae sample produced in accordance with the present invention is set forth.

Sample #: 61562-001
Sample Description: Freeze Dry Golden Brown Algae
Temp on Receipt: RT
Comment: Fatty Acid Profile (P005) was subcontracted to another qualified testing laboratoriy

| Test | Compound | Specification Limit | Result | Detection Limit |
|---|---|---|---|---|
| Chlorophyll | | | 360 mg/100 g | |
| Carotenoid Esters - total | | | 0.66% | |
| Total Polyphenols - UV | Total polyphenols | | 7.9% | n/a |
| Vitamin A - assay | Beta-carotene mcg divided by 6 | | 72 RE/100 g | <10 IU/100 g, |
| | Retinol | | ND RE/100 g | <10 IU/100 g, |
| | Total vitamin A | | 72 RE/100 g | <10 IU/100 g, |
| Vitamin C - assay | | | 128.9 mg/g | 5 ppm |
| | or | | 12.8% | |
| Vitamin D assay | | | ND | 10 IU/100 g |
| Vitamin E - assay | | | ND | 0.1 mg/100 g |
| Vitamin Test | B1 - Thiamine | | 0.16 mg/100 g | 0.1 mg/100 g |
| | B2 - Riboflavin | | 0.43 mg/100 g | 0.1 mg/100 g |
| | B3 - Niacin | | 1.56 mg/100 g | 0.1 mg/100 g |
| | B5 - Calcium D-Pantothenate | | 0.33 mg/100 g | 0.1 mg/100 g |
| | B6 - Pyridoxine HCl | | 0.18 mg/100 g | 0.1 mg/100 g |
| Fatty Acid Profile - nutritional | Trans Fat | | <0.01% | 0.1% |
| | Fat as Triglyceride | | 3.03% | 0.1% |
| | Saturated Fatty Acids | | 1.09% | 0.1% |
| amino acid screen (AMINO-CMPL) | alanine | | 1.25% | 0.10% |
| | arginine | | 1.36% | 0.10% |
| | aspartic acid | | 1.78% | 0.10% |
| | glutamic acid | | 2.28% | 0.10% |
| | glycine | | 0.97% | 0.10% |
| | histidine | | 0.43% | 0.10% |
| | isoleucine | | 0.90% | 0.10% |
| | leucine | | 1.42% | 0.10% |
| | lysine | | 0.64% | 0.10% |
| Metal analysis by ICP/MS (trace) | Molybdenum | | 0.13 ppm | 0.01 ppm |
| | Nickel | | 0.09 ppm | 0.02 ppm |
| | Phosphorus | | 117 ppm | 1 ppm |

-continued

Sample #: 61562-001
Sample Description: Freeze Dry Golden Brown Algae
Temp on Receipt: RT
Comment: Fatty Acid Profile (P005) was subcontracted to another qualified testing laboratoriy

| Test | Compound | Specification Limit | Result | Detection Limit |
|---|---|---|---|---|
| | Potassium | | 205 ppm | 0.5 ppm |
| | Selenium | | <0.04 ppm | 0.04 ppm |
| | Silver | | 1.47 ppm | 0.02 ppm |
| | Sodium | | 7.42 mg/g | 1 ppm |
| | Strontium | | 8.29 ppm | 0.01 ppm |
| | Thallium | | 0.29 ppm | 0.01 ppm |
| | Thorium | | 1.24 ppm | 0.01 ppm |
| | Tin | | 0.43 ppm | 0.01 ppm |
| | Titanium | | 0.82 ppm | 0.02 ppm |
| | Uranium | | 0.53 ppm | 0.01 ppm |
| | Vanadium | | 0.16 ppm | 0.01 ppm |
| | Zinc | | <0.05 ppm | 0.05 ppm |
| | Zirconium | | 1.80 ppm | 0.01 ppm |
| amino acid screen (AMINO-CMPL) | phenylalanine | | 0.95% | 0.10% |
| | proline | | 0.59% | 0.10% |
| | serine | | 0.84% | 0.10% |
| | threonine | | 0.83% | 0.10% |
| | tryptophan | | 0.20% | 0.10% |
| | tyrosine | | 0.67% | 0.10% |
| | valine | | 0.88% | 0.10% |
| Amylase - alpha | | | No activity detected | |
| Lipase | | | No activity detected LU | |
| Proteolytic activity, bacterial source | | | 6.3 PC units/g | |
| Vitamin B12 (microbial) | | | 9.6 mcg/100 g | |
| Metal analysis by ICP/MS (trace) | Aluminum | | <0.1 ppm | 0.1 ppm |
| | Antimony | | 0.03 ppm | 0.01 ppm |
| | Arsenic | | <0.01 ppm | 0.01 ppm |
| | Barium | | 0.73 ppm | 0.02 ppm |
| | Beryllium | | 0.12 ppm | 0.01 ppm |
| | Bismuth | | 0.21 ppm | 0.02 ppm |
| | Boron | | 5.76 ppm | 0.2 ppm |
| | Cadmium | | <0.001 ppm | 0.001 ppm |
| | Calcium | | 156 ppm | 1.0 ppm |
| | Chromium | | <0.02 ppm | 0.02 ppm |
| | Cobalt | | 0.28 ppm | 0.01 ppm |
| | Copper | | 1.24 ppm | 0.01 ppm |
| | Iron | | 1.90 ppm | 0.5 ppm |
| | Lead | | 0.22 ppm | 0.01 ppm |
| | Lithium | | 0.73 ppm | 0.05 ppm |
| | Magnesium | | 731 ppm | 0.02 ppm |
| | Manganese | | 0.38 ppm | 0.02 ppm |
| | Mercury | | 0.086 ppm | 0.005 ppm |

Vitamin A - assay - H081f - Vitamin A and Beta Carotene in Food Products based on AOAC Method 970.64
Vitamin B1, B2, B3, B5, B6 package - AOAC 961.15(modified) - analysis by LC/MS/MS
Vitamin B12 (microbial) - USP 31 <171> modified for food
Vitamin C - assay - Vitamin C in Food Products based on Extraction by AOAC Methods of Analysis for Nutrition Labeling (1993) Chapter 37, Analysis by HPLC
Vitamin D assay - AOAC Method of Analysis for Nutrition Labeling (1993) Chapter 38
Vitamin E - assay - AOAC Method of Analysis for Nutrition Labeling (1993) Chapter 39, modified
Methodology:
amino acid screen (AMINO-CMPL) - USDA 6.011 (1986)
Amylase - alpha - FCC UV Spectraphotometry
Carotenoid Esters - total - UV Absorption
Chlorophyll - AOAC
Fatty Acid Profile - nutritional - P005 - Fatty Acid Profile in Food Products based on AOAC 996.06, AOCS Official Method Ce2-66
Lipase - FCC 4th edition (titration)
Metal analysis by ICP/MS (trace) - AOAC 984.27 using ICP/MS
Total Polyphenols - UV - Colorimeteric - using Folin-Clocalteu reagent

Example 3

A compositional analysis of a dehydrated Golden Brown Algae sample produced in accordance with the present invention is set forth.

Sample #: 61562-002  
Sample Description: Dehydrated Golden Brown Algae  
Temp on Receipt: RT  
Comment: Fatty Acid Profile (P005) was subcontracted to another qualified testing laboratoriy

| Test | Compound | Specification Limit | Result | Detection Limit |
|---|---|---|---|---|
| Chlorophyll | | | 411 mg/100 g | |
| Carotenoid Esters - total | | | 0.63% | |
| Total Polyphenols - UV | Total polyphenols | | 8.9% | n/a |
| Vitamin A - assay | Beta-carotene mcg divided by 6 | | 1922 RE/100 g | <10 IU/100 g, |
| | Retinol | | ND RE/100 g | <10 IU/100 g, |
| | Total vitamin A | | 1922 RE/100 g | <10 IU/100 g, |
| Vitamin C - assay | | | 126.0 mg/g | 5 ppm |
| | or | | 12.6% | |
| Vitamin D assay | | | ND | 10 IU/100 g |
| Vitamin E - assay | | | ND | 0.1 mg/100 g |
| Vitamin Test | B1 - Thiamine | | 0.13 mg/100 g | 0.1 mg/100 g |
| | B2 - Riboflavin | | 0.30 mg/100 g | 0.1 mg/100 g |
| | B3 - Niacin | | 0.65 mg/100 g | 0.1 mg/100 g |
| | B5 - Calcium D-Pantothenate | | 0.09 mg/100 g | 0.1 mg/100 g |
| | B6 - Pyridoxine HCl | | 0.11 mg/100 g | 0.1 mg/100 g |
| Fatty Acid Profile - nutritional | Fat as Triglyceride | | 3.08% | 0.1% |
| | Trans Fat | | <0.01% | 0.1% |
| | Saturated Fatty Acids | | 0.65% | 0.1% |
| amino acid screen (AMINO-CMPL) | alanine | | 1.20% | 0.10% |
| | arginine | | 1.22% | 0.10% |
| | aspartic acid | | 1.84% | 0.10% |
| | glutamic acid | | 2.27% | 0.10% |
| | glycine | | 0.99% | 0.10% |
| | histidine | | 0.37% | 0.10% |
| | isoleucine | | 0.96% | 0.10% |
| | leucine | | 1.44% | 0.10% |
| | lysine | | 0.47% | 0.10% |
| amino acid screen (AMINO-CMPL) | phenylalanine | | 1.01% | 0.10% |
| | proline | | 0.59% | 0.10% |
| | serine | | 0.82% | 0.10% |
| | threonine | | 0.83% | 0.10% |
| | tryptophan | | 0.23% | 0.10% |
| | tyrosine | | 0.68% | 0.10% |
| | valine | | 0.91% | 0.10% |
| Amylase - alpha | | | No activity detected | |
| Lipase | | | 8.2 LU/g | |
| Proteolytic activity, bacterial source | | | 1.3 PC units/g | |
| Vitamin B12 (microbial) | | | 4.7 mcg/100 g | |
| Metal analysis by ICP/MS (trace) | Aluminum | | <0.1 ppm | 0.1 ppm |
| | Antimony | | <0.01 ppm | 0.01 ppm |
| | Arsenic | | <0.01 ppm | 0.01 ppm |
| | Barium | | 0.33 ppm | 0.02 ppm |
| | Beryllium | | 0.11 ppm | 0.01 ppm |
| | Bismuth | | 0.19 ppm | 0.02 ppm |
| | Boron | | 1.93 ppm | 0.2 ppm |
| | Cadmium | | <0.001 ppm | 0.001 ppm |
| | Calcium | | 54.9 ppm | 1.0 ppm |
| | Chromium | | <0.02 ppm | 0.02 ppm |
| | Cobalt | | 0.25 ppm | 0.01 ppm |
| | Copper | | 0.59 ppm | 0.01 ppm |
| | Iron | | <0.5 ppm | 0.5 ppm |
| | Lead | | 0.19 ppm | 0.01 ppm |
| | Lithium | | 0.17 ppm | 0.05 ppm |
| | Magnesium | | 242 ppm | 0.02 ppm |
| | Manganese | | 0.14 ppm | 0.02 ppm |
| | Mercury | | 0.065 ppm | 0.005 ppm |
| Metal analysis by ICP/MS (trace) | Molybdenum | | 0.02 ppm | 0.01 ppm |
| | Nickel | | 0.07 ppm | 0.02 ppm |
| | Phosphorus | | 34.2 ppm | 1 ppm |
| | Potassium | | 66.2 ppm | 0.5 ppm |
| | Selenium | | <0.04 ppm | 0.04 ppm |
| | Silver | | 1.37 ppm | 0.02 ppm |
| | Sodium | | 2.72 mg/g | 1 ppm |
| | Strontium | | 3.59 ppm | 0.01 ppm |
| | Thallium | | 0.27 ppm | 0.01 ppm |
| | Thorium | | 1.12 ppm | 0.01 ppm |
| | Tin | | 0.32 ppm | 0.01 ppm |
| | Titanium | | 0.02 ppm | 0.02 ppm |
| | Uranium | | 0.38 ppm | 0.01 ppm |
| | Vanadium | | 0.13 ppm | 0.01 ppm |

-continued

Sample #: 61562-002
Sample Description: Dehydrated Golden Brown Algae
Temp on Receipt: RT
Comment: Fatty Acid Profile (P005) was subcontracted to another qualified testing laboratoriy

| Test | Compound | Specification Limit | Result | Detection Limit |
|---|---|---|---|---|
| | Zinc | | <0.05 ppm | 0.05 ppm |
| | Zirconium | | 1.48 ppm | 0.01 ppm |

Methodology:
amino acid screen (AMINO-CMPL) - USDA 6.011 (1986)
Amylase - alpha - FCC UV Spectraphotometry
Carotenoid Esters - total - UV Absorption
Chlorophyll - AOAC
Fatty Acid Profile - nutritional - P005 - Fatty Acid Profile in Food Products based on AOAC 996.06, AOCS Official Method Ce2-66
Lipase - FCC 4th edition (titration)
Metal analysis by ICP/MS (trace) - AOAC 984.27 using ICP/MS
Total Polyphenols - UV - Colorimeteric - using Folin-Ciocalteu reagent
Vitamin A - assay - H081f - Vitamin A and Beta Carotene in Food Products based on AOAC Method 970.64
Vitamin B1, B2, B3, B5, B6 package - AOAC 961.15(modified) - analysis by LC/MS/MS
Vitamin B12 (microbial) - USP 31 <171> modified for food
Vitamin C - assay - Vitamin C in Food Products based on Extraction by AOAC Methods of Analysis for Nutrition Labeling (1993) Chapter 37, Analysis by HPLC
Vitamin D assay - AOAC Method of Analysis for Nutrition Labeling (1993) Chapter 38
Vitamin E - assay - AOAC Method of Analysis for Nutrition Labeling (1993) Chapter 39, modified

Example 4

A compositional analysis of a Golden Brown Marine Phytoplankton (A/B) Brown Liquid sample produced in accordance with the present invention is set forth.

Results of Analysis

Golden Brown Marine Phytoplankton (NB) Brown Liquid; Lot #1:1-012208-A

Report of Fatty Acid Profile

| Type of fatty acid | % of fatty acid in sample |
|---|---|
| saturated | 0.01% |
| cis-monounsaturated | 0.01% |
| cis-polyunsaturated | 0.01% |
| total fatty acid as triglyceride | 0.02% |
| total Omega 3 | 0.01% |
| total Omega 6 | 0.00% |
| total trans(18:1, 18:2) | 0.00% |

| Component Name | Carbon Chain | % of total fatty acid |
|---|---|---|
| caproic acid | C6:0 | 0.54 |
| caprylic acid | C8:0 | 0.18 |
| capric acid | C10:0 | 0.08 |
| undecanoic acid | C11:0 | 0.00 |
| lauric acid | C12:0 | 0.26 |
| tridecanoic acid | C13:0 | 0.00 |
| myristoleic acid | C14:1 | 0.30 |
| myristic acid | C14:0 | 13.15 |
| pentadecenoic acid | C15:1 | 0.09 |
| pentadecanoic acid | C15:0 | 1.00 |
| palmitoleic acid | C16:1 | 24.03 |
| palmitic acid | C16:0 | 19.65 |
| cis-10-heptadecenoic | C17:1 | 0.00 |
| heptadecanoic acid | C17:0 | 0.13 |
| gama-linolenic acid | C18:3 | 0.00 |
| linoleic acid | C18:2c | 2.13 |
| linolenic acid | C18:3 | 1.13 |
| oleic acid | C18:1c | 2.29 |
| linolelaidic acid | C18:2t | 0.00 |
| elaidic acid | C18:1t | 3.64 |
| stearic acid | C18:0 | 1.16 |
| vaccinnic acid | C18:1cis-11 | 0.41 |
| octadecanoic acid | C18:1trans-11 | 0.00 |
| arachidonic acid | C20:4 | 6.91 |
| eicosapentaenoic acid | C20:5 | 17.47 |
| eicosatrienoic acid | C20:3n6 | 0.00 |
| eicosadienoic acid | C20:2 | 0.00 |
| eicosenoic acid | C20:1 | 0.00 |
| eicosatrienoic acid | C20:3n3 | 0.00 |
| arachidic acid | C20:0 | 0.41 |
| heneicosanoic acid | C21:0 | 0.00 |
| docosahexaenoic acid | C22:6 | 4.05 |
| docosapentaenoic acid | C22:5 | 0.34 |
| docosadienoic acid | C22:2 | 0.00 |
| erucic acid | C22:1 | 0.00 |
| behenic acid | C22:0 | 0.41 |
| tricosanoic acid | C23:0 | 0.00 |
| nervonic acid | C24:1 | 0.00 |
| lignoceric acid | C24:0 | 0.24 |

Results of Analysis

Golden Brown Marine Phytoplankton (A/F) Clear Liquid; Lot #1:1-012208-G

Report of Fatty Acid Profile

| Type of fatty acid | % of fatty acid in sample |
|---|---|
| saturated | 0.001% |
| cis-monounsaturated | 0.000% |
| cis-polyunsaturated | 0.000% |
| total fatty acid as triglyceride | 0 002% |
| total Omega 3 | 0.000% |
| total Omega 6 | 0.000% |
| total trans(18:1, 18:2) | 0.000% |

| Component Name | Carbon Chain | % of total fatty acid |
|---|---|---|
| caproic acid | C6:0 | 0.00 |
| caprylic acid | C8:0 | 0.51 |
| capric acid | C10.0 | 0.00 |
| undecanoic acid | C11.0 | 0.00 |
| lauric acid | C12:0 | 1.79 |

| | | |
|---|---|---|
| tridecanoic acid | C13:0 | 0.00 |
| myristoleic acid | C14:1 | 0.00 |
| myristic acid | C14:0 | 10.63 |
| pentadecenoic acid | C15:1 | 0.00 |
| pentadecanoic acid | C15:0 | 0.00 |
| palmitoleic acid | C16:1 | 1.54 |
| palmitic acid | C16:0 | 44.48 |
| cis-10-heptadecenoic | C17:1 | 0.00 |
| heptadecanoic acid | C17:0 | 0.00 |
| gama-linolenic acid | C18:3 | 0.00 |
| linoleic acid | C18:2c | 0.00 |
| linolenic acid | C18:3 | 0.00 |
| oleic acid | C18:1c | 15.77 |
| linolelaidic acid | C18:2t | 0.00 |
| elaidic acid | C18:1t | 8.34 |
| stearic acid | C18:0 | 0.00 |
| vaccinnic acid | C18:1cis-11 | 0.00 |
| octadecanoic acid | C18:1trans-11 | 0.00 |
| arachidonic acid | C20:4 | 0.00 |
| eicosapentaenoic acid | C20:5 | 0.00 |
| eicosatrienoic acid | C20:3n6 | 0.00 |
| eicosadienoic acid | C20:2 | 0.00 |
| eicosenoic acid | C20:1 | 0.00 |
| eicosatrienoic acid | C20:3n3 | 0.00 |
| arachidic acid | C20:0 | 0.00 |
| heneicosanoic acid | C21:0 | 0.00 |
| docosahexaenoic acid | C22:6 | 11.81 |
| docosapentaenoic acid | C22:5 | 0.00 |
| docosadienoic acid | C22:2 | 0.00 |
| erucic acid | C22:1 | 0.00 |
| behenic acid | C22:0 | 3.34 |
| tricosanoic acid | C23:0 | 0.00 |
| nervonic acid | C24:1 | 0.00 |
| lignoceric acid | C24:0 | 1.80 |

Example 5

A compositional analysis of another Golden Brown Marine Phytoplankton (A/B) Brown Liquid sample produced in accordance with the present invention is set forth.

Sample #: 58773-001
Sample Description: Golden Brown Marine Phytoplankton (A/B) Brown Liquid; Lot# 1:1-012208-A
Temp on Receipt: 9° C.
Comment: ND = not detected

| Test | Compound | Specification Limit | Result | Detection Limit |
|---|---|---|---|---|
| Chlorophyll | | | 39.4 mg/L | |
| Fat extraction for fatty acids | | | <0.4% | 0.4% |
| Carotenoid Esters - total | | | 0.03% | n/a |
| Total Polyphenols - UV | Total polyphenols | | 0.122% | n/a |
| Vitamin A - assay | Beta-carotene mcg divided by 6 | | ND | <10 IU/100 g, |
| | Retinol | | ND | <10 IU/100 g, |
| | Total vitamin A | | ND | <10 IU/100 g, |
| Vitamin C - assay | | | 153 mg/100 g | 0.5 mg/100 g |
| Vitamin D assay | | | ND | 10IU/100 g |
| Vitamin E - assay | | | ND | 0.1 mg/100 g |
| Vitamin Test | B1 - Thiamine | | ND | 0.1 mg/100 g |
| | B2 - Riboflavin | | 0.026 mg/100 g | 0.1 mg/100 g |
| | B3 - Niacin | | 0.21 mg/100 g | 0.1 mg/100 g |
| | B5 - Calcium D-Pantothenate | | ND | 0.1 mg/100 g |
| | B6 - Pyridoxine | | ND | 0.1 mg/100 g |
| Fatty Acid Profile | | | see attached % | |
| amino acid screen (complete profile) | Tryptophane | | <0.01% | 0.05% |
| | Aspartic Acid | | 0.02% | 0.05% |
| | Alanine | | <0.01% | 0.10% |
| | Arginine | | 0.03% | 0.10% |
| | Cystine | | 0.08% | 0.10% |
| | Glutamic Acid | | 0.01% | 0.10% |
| | Glycine | | 0.01% | 0.10% |
| | Histidine | | 0.02% | 0.10% |
| | Hydroxyproline | | <0.01% | 0.10% |
| | Isoleucine | | 0.01% | 0.10% |
| | Leucine | | 0.02% | 0.10% |
| amino acid screen (complete profile) | Lysine | | 0.01% | 0.10% |
| | Methionine | | <0.01% | 0.10% |
| | Phenylalanine | | 0.01% | 0.10% |
| | Proline | | <0.01% | 0.10% |
| | Serine | | 0.01% | 0.10% |
| | Threonine | | 0.01% | 0.10% |
| | Tyrosine | | <0.01% | 0.10% |
| | Valine | | 0.01% | 0.10% |
| Amylase - alpha | | | 0 DU/ml | |
| Lipase | | | 0 LY/ml | |
| Proteolytic activity, bacterial source | | | 0 PC/ml | |
| Vitamin B12 (bioassay) | | | 0.55 mcg/100 g | |
| Metal analysis by ICP/MS (trace) | Aluminum | | 0.86 ppm | 0.1 ppm |
| | Antimony | | <0.01 ppm | 0.01 ppm |
| | Arsenic | | 0.05 ppm | 0.01 ppm |
| | Barium | | <0.02 ppm | 0.02 ppm |

-continued

Sample #: 58773-001
Sample Description: Golden Brown Marine Phytoplankton (A/B) Brown Liquid; Lot# 1:1-012208-A
Temp on Receipt: 9° C.
Comment: ND = not detected

| Test | Compound | Specification Limit | Result | Detection Limit |
|---|---|---|---|---|
| | Beryllium | | <0.01 ppm | 0.01 ppm |
| | Bismuth | | <0.02 ppm | 0.02 ppm |
| | Phosphorus | | 0.84 ppm | 1 ppm |
| | Boron | | 0.45 ppm | 0.2 ppm |
| | Cadmium | | <0.001 ppm | 0.001 ppm |
| | Calcium | | <1 ppm | 1.0 ppm |
| | Chromium | | <0.02 ppm | 0.02 ppm |
| | Cobalt | | <0.01 ppm | 0.01 ppm |
| | Copper | | 0.05 ppm | 0.01 ppm |
| | Iron | | <0.5 ppm | 0.5 ppm |
| | Lead | | <0.01 ppm | 0.01 ppm |
| | Lithium | | <0.05 ppm | 0.05 ppm |
| Metal analysis by ICP/MS (trace) | Magnesium | | 119 ppm | 0.02 ppm |
| | Manganese | | <0.02 ppm | 0.02 ppm |
| | Mercury | | 0.006 ppm | 0.005 ppm |
| | Molybdenum | | <0.01 ppm | 0.01 ppm |
| | Nickel | | <0.02 ppm | 0.02 ppm |
| | Potassium | | 108 ppm | 0.5 ppm |
| | Selenium | | <0.04 ppm | 0.04 ppm |
| | Silver | | <0.02 ppm | 0.02 ppm |
| | Sodium | | 1.0 mg/ml | 1 ppm |
| | Strontium | | <0.01 ppm | 0.01 ppm |
| | Thallium | | <0.01 ppm | 0.01 ppm |
| | Thorium | | 0.15 ppm | 0.01 ppm |
| | Tin | | 0.02 ppm | 0.01 ppm |
| | Titanium | | <0.02 ppm | 0.02 ppm |
| | Uranium | | 0.10 ppm | 0.01 ppm |
| | Vanadium | | <0.01 ppm | 0.01 ppm |
| | Zinc | | 0.63 ppm | 0.05 ppm |
| | Zirconium | | 0.03 ppm | 0.01 ppm |

Methodology:
amino acid screen (complete profile) - USDA 6.011 (1986)
Amylase - alpha - FCC UV Spectraphotometry
Carotenoid Esters - total - UV Absorption
Chlorophyll - AOAC
Fat extraction for fatty acids - C101b - Fat in Foods by Hydrolytic Extraction based on AOAC Method 996.06
Fatty Acid Profile - P005 - Fatty Acid Profile in Food Products based on AOAC 996.06, AOCS Official Method Ce2-66
Lipase - FCC 4th edition (titration)
Metal analysis by ICP/MS (trace) - ICP/MS
Total Polyphenols - UV - Colorlmeteric - using Folin-Ciocalteu reagent
Vitamin A - assay - H081f - Vitamin A and Beta Carotene in Food Products based on AOAC Method of Analysis for Nutrition Labeling (1993) Chapter 36 modified
Vitamin B1, B2, B3, B5, B6 package - LC/MS/MS - in house
Vitamin B12 (bioassay) - USP 30 <171> modified for food
Vitamin C - assay - Vitamin C in Food Products based on Extraction by AOAC Methods of Analysis for Nutrition Labeling (1993) Chapter 37, Analysis by HPLC
Vitamin D assay - AOAC Method of Analysis for Nutrition Labeling (1993) Chapter 38
Vitamin E - assay - AOAC Method of Analysis for Nutrition Labeling (1993) Chapter 39, modified Example 6

A compositional analysis of a Golden Brown Marine Phytoplankton (A/F) Clear Liquid sample produced in accordance with the present invention is set forth.

Sample #: 58773-002
Sample Description: Golden Brown Marine Phytoplankton (A/F) Clear Liquid; Lot# 1:1-012208-G
Temp on Receipt: 9° C.
Comment: ND = not detected

| Test | Compound | Specification Limit | Result | Detection Limit |
|---|---|---|---|---|
| Chlorophyll | | | 0.32 mg/L | |
| Fat extraction for fatty acids | | | <0.4% | 0.4% |
| Carotenoid Esters - total | | | 0.01% | n/a |
| Total Polyphenols - UV | Total polyphenols | | 0.13% | n/a |
| Vitamin A - assay | Beta-carotene mcg | | ND | <10 IU/100 g, |

-continued

Sample #: 58773-002
Sample Description: Golden Brown Marine Phytoplankton (A/F) Clear Liquid; Lot# 1:1-012208-G
Temp on Receipt: 9° C.
Comment: ND = not detected

| Test | Compound | Specification Limit | Result | Detection Limit |
|---|---|---|---|---|
| | divided by 6 | | | |
| | Retinol | | ND | <10 IU/100 g, |
| | Total vitamin A | | ND | <10 IU/100 g, |
| Vitamin C - assay | | | 176 mg/100 g | 0.5 mg/100 g |
| Vitamin D assay | | | ND | 10 IU/100 g |
| Vitamin E - assay | | | ND | 0.1 mg/100 g |
| Vitamin Test | B1 - Thiamine | | ND | 0.1 mg/100 g |
| | B2 - Riboflavin | | 0.020 mg/100 g | 0.1 mg/100 g |
| | B3 - Niacin | | 0.162 mg/100 g | 0.1 mg/100 g |
| | B5 - Calcium D-Pantothenate | | ND | 0.1 mg/100 g |
| | B6 - Pyridoxine | | ND | 0.1 mg/100 g |
| Fatty Acid Profile | | | see attached % | |
| amino acid screen (complete profile) | Aspartic Acid | | 0.02% | 0.05% |
| | Proline | | <0.01% | 0.05% |
| | Tryptophan | | <0.01% | 0.05% |
| | Alanine | | 0.03% | 0.10% |
| | Arginine | | 0.03% | 0.10% |
| | Cystine | | 0.06% | 0.10% |
| | Glutamic Acid | | 0.01% | 0.10% |
| | Glycine | | 0.01% | 0.10% |
| | Histidine | | <0.01% | 0.10% |
| | Hydroxyproline | | <0.01% | 0.10% |
| | Isoleucine | | 0.01% | 0.10% |
| amino acid screen (complete profile) | Leucine | | 0.01% | 0.10% |
| | Lysine | | 0.01% | 0.10% |
| | Methionine | | 0.01% | 0.10% |
| | Phenylalanine | | 0.01% | 0.10% |
| | Serine | | <0.01% | 0.10% |
| | Threonine | | <0.01% | 0.10% |
| | Tyrosine | | <0.01% | 0.10% |
| | Valine | | <0.01% | 0.10% |
| Amylase - alpha | | | 0 DU/ml | |
| Lipase | | | 0 LY/ml | |
| Proteolytic activity, bacterial source | | | 0 PC/ml | |
| Vitamin B12 (bioassay) | | | <0.2 mcg/100 g | |
| Metal analysis by ICP/MS (trace) | Aluminum | | 0.83 ppm | 0.1 ppm |
| | Antimony | | <0.01 ppm | 0.01 ppm |
| | Arsenic | | 0.05 ppm | 0.01 ppm |
| | Barium | | <0.02 ppm | 0.02 ppm |
| | Beryllium | | <0.01 ppm | 0.01 ppm |
| | Bismuth | | <0.02 ppm | 0.02 ppm |
| | Phospohorus | | 0.28 ppm | 1 ppm |
| | Boron | | 0.32 ppm | 0.2 ppm |
| | Cadmium | | <0.001 ppm | 0.001 ppm |
| | Calcium | | 0.73 ppm | 1.0 ppm |
| | Chromium | | <0.02 ppm | 0.02 ppm |
| | Cobalt | | <0.01 ppm | 0.01 ppm |
| | Copper | | 0.06 ppm | 0.01 ppm |
| | Iron | | <0.5 ppm | 0.5 ppm |
| | Lead | | <0.01 ppm | 0.01 ppm |
| | Lithium | | <0.05 ppm | 0.05 ppm |
| Metal analysis by ICP/MS (trace) | Magnesium | | 94.7 ppm | 0.02 ppm |
| | Manganese | | <0.02 ppm | 0.02 ppm |
| | Mercury | | 0.006 ppm | 0.005 ppm |
| | Molybdenum | | <0.01 ppm | 0.01 ppm |
| | Nickel | | <0.02 ppm | 0.02 ppm |
| | Potassium | | 89.4 ppm | 0.5 ppm |
| | Selenium | | <0.04 ppm | 0.04 ppm |
| | Silver | | <0.02 ppm | 0.02 ppm |
| | Sodium | | 863 ppm | 1 ppm |
| | Strontium | | <0.01 ppm | 0.01 ppm |
| | Thallium | | <0.01 ppm | 0.01 ppm |
| | Thorium | | 0.16 ppm | 0.01 ppm |
| | Tin | | 0.04 ppm | 0.01 ppm |
| | Titanium | | <0.02 ppm | 0.02 ppm |
| | Uranium | | 0.10 ppm | 0.01 ppm |

Sample #: 58773-002
Sample Description: Golden Brown Marine Phytoplankton (A/F) Clear Liquid; Lot# 1:1-012208-G
Temp on Receipt: 9° C.
Comment: ND = not detected

| Test | Compound | Specification Limit | Result | Detection Limit |
|---|---|---|---|---|
| | Vanadium | | <0.01 ppm | 0.01 ppm |
| | Zinc | | 0.30 ppm | 0.05 ppm |
| | Zirconium | | 0.04 ppm | 0.01 ppm |

Methodology:
amino acid screen (complete profile) - USDA 6.011 (1986)
Amylase - alpha - FCC UV Spectraphotometry
Carotenoid Esters - total - UV Absorption
Chlorophyll - AOAC
Fat extraction for fatty acids - C101b - Fat in Foods by Hydrolytic Extraction based on AOAC Method 996.06
Fatty Acid Profile - P005 - Fatty Acid Profile in Food Products based on AOAC 996.06, AOCS Official Method Ce2-66
Lipase - FCC 4th edition (titration)
Metal analysis by ICP/MS (trace) - ICP/MS
Total Polyphenols - UV - Colorimeteric - using Folin-Ciocalteu reagent
Vitamin A - assay - H081f - Vitamin A and Beta Carotene in Food Products based on AOAC Method of Analysis for Nutrition Labeling (1993) Chapter 36 modified
Vitamin B1, B2, B3, B5, B6 package - LC/MS/MS - in house
Vitamin B12 (bioassay) - USP 30 <171> modified for food
Vitamin C - assay - Vitamin C in Food Products based on Extraction by AOAC Methods of Analysis for Nutrition Labeling (1993) Chapter 37, Analysis by HPLC
Vitamin D assay - AOAC Method of Analysis for Nutrition Labeling (1993) Chapter 38
Vitamin E - assay - AOAC Method of Analysis for Nutrition Labeling (1993) Chapter 39, modified

Example 7

A compositional analysis of an algae sample (ID#: US100-54133) produced in accordance with the present invention is set forth.

Results of Analysis

Algae Sample

Report of Fatty Acid Profile

| Type of fatty acid | % of fatty acid in sample |
|---|---|
| saturated | 0.92% |
| cis-monounsaturated | 0.61% |
| cis-polyunsaturated | 1.75% |
| total fat | 3.29% |
| total Omega 3 | 1.52% |
| total Omega 6 | 0.18% |
| total trans(18:1, 18:2) | 0.01% |

| Component Name | Carbon Chain | % of total fatty acid |
|---|---|---|
| caproic acid | C6:0 | 0.000 |
| caprylic acid | C8:0 | 0.000 |
| capric acid | C10.0 | 0.202 |
| undecanoic acid | C11.0 | 0.000 |
| lauric acid | C12:0 | 0.532 |
| tridecanoic acid | C13:0 | 0.000 |
| myristoleic acid | C14:1 | 1.755 |
| myristic acid | C14:0 | 5.926 |
| pentadecenoic acid | C15:1 | 0.328 |
| pentadecanoic acid | C15:0 | 0.469 |
| palmitoleic acid | C16:1 | 8.787 |
| palmitic acid | C16:0 | 18.136 |
| cis-10-heptadecenoic | C17:1 | 0.000 |
| heptadecanoic acid | C17:0 | 0.000 |
| gama-linolenic acid | C18:3 | 0.000 |
| linoleic acid | C18:2c | 4.990 |
| linolenic acid | C18:3 | 1.422 |
| oleic acid | C18:1c | 6.263 |
| linoielaidic acid | C18:2t | 0.000 |
| elaidic acid | C18:1t | 0.294 |
| stearic acid | C18:0 | 2.468 |
| vaccinnic acid | C18:1cis-11 | 1.275 |
| octadecanoic acid | C18:1trans-11 | 0.000 |
| arachidonic acid | C20:4 | 0.371 |
| eicosapentaenoic acid | C20:5 | 36.055 |
| eicosatrienoic acid | C20:3n6 | 0.000 |
| eicosadienoic acid | C20:2 | 1.619 |
| eicosenoic acid | C20:1 | 0.000 |
| eicosatrienoic acid | C20:3n3 | 0.000 |
| arachidic acid | C20:0 | 0.000 |
| heneicosanoic acid | C21:0 | 0.000 |
| docosahexaenoic acid | C22:6 | 8.743 |
| docosapentaenoic acid | C22:5 | 0.000 |
| docosadienoic acid | C22:2 | 0.000 |
| erucic acid | C22:1 | 0.000 |
| behenic acid | C22:0 | 0.365 |
| tricosanoic acid | C23:0 | 0.000 |
| nervonic acid | C24:1 | 0.000 |
| lignoceric acid | C24:0 | 0.000 |

Example 8

A compositional analysis of a Golden Brown Algae (14.89% Moisture Content) sample produced in accordance with the present invention is set forth.

Sample #: 62510-002
Sample Description: Golden Brown Algae, Processed at MCD Tech, 14.89% moisture content/8 mesh
Temp on Receipt: RT
Comment: ND = not detected or less than detection limit

| Test | Compound | Specification Limit | Result | Detection Limit |
|---|---|---|---|---|
| Chlorophyll | | | 552.4 mg/100 g | |
| Carotenoid Esters - total | | | 0.61% | |
| Total Polyphenols - UV | Total polyphenols | | 4.3% | n/a |
| Vitamin A - assay | Beta-carotene mcg divided by 6 | | 2224 RE/100 g | <10 IU/100 g, |
| | Retinol | | ND | <10 IU/100 g, |
| | Total vitamin A | | 2224 RE/100 g | <10 IU/100 g, |
| Vitamin C - assay | Vitamin C | | 1.8 g/100 g | 5 ppm |
| Vitamin D assay | VD3 | | ND | 10 IU/100 g, |
| | VD2 | | ND | 10 IU/100 g |
| Vitamin E - assay | gamma-Tocopherol | | 81.1 mg/100 g | 0.1 mg/100 g |
| Vitamin Test | B1 - Thiamine | | ND | 0.1 mg/100 g |
| | B2 - Riboflavin | | 0.22 mg/100 g | 0.1 mg/100 g |
| | B3 - Niacin | | 0.67 mg/100 g | 0.1 mg/100 g |
| | B5 - Calcium D-Pantothenate | | ND | 0.1 mg/100 g |
| | B6 - Pyridoxine HCl | | ND | 0.1 mg/100 g |
| Fatty Acid Profile - nutritional | cis-Monounsaturated Fatty Acids | | 0.80% | 0.1% |
| | Omega-3 Fatty Acids | | 1.36% | 0.1% |
| | cis-Polyunsaturated fatty Acids | | 2.02% | 0.1% |
| | Conjugated Fatty Acids | | <0.01% | 0.1% |
| | Omega-6 Fatty Acids | | 0.12% | 0.1% |
| | Saturated fatty acids | | 1.11% | 0.1% |
| | Trans fatty acids | | 0.02% | 0.01% |
| | Fat as Triglycerides | | 4.14% | 0.1% |
| amino acid screen (AMINO-CMPL) | alanine | | 1.42% | 0.10% |
| | arginine | | 1.27% | 0.10% |
| | aspartic acid | | 2.34% | 0.10% |
| | cystine | | 0.54% | 0.10% |
| | glutamic acid | | 2.47% | 0.10% |
| | glycine | | 1.26% | 0.10% |
| | histidine | | 0.44% | 0.10% |
| | hydroxyproline | | <0.01% | 0.10% |
| | isoleucine | | 1.10% | 0.10% |
| | leucine | | 1.92% | 0.10% |
| | lysine | | 1.11% | 0.10% |
| | methionine | | 0.74% | 0.10% |
| | phenylalanine | | 1.31% | 0.10% |
| | proline | | 0.34% | 0.10% |
| | serine | | 1.17% | 0.10% |
| | threonine | | 0.96% | 0.10% |
| | tryptophan | | 0.16% | 0.10% |
| | tyrosine | | 0.82% | 0.10% |
| | valine | | 1.25% | 0.10% |
| Amylase - alpha | | | <200 BAU/g | |
| Lipase | | | No activity detected LU/g | |
| Proteolytic activity, bacterial source | | | No Activity detected PC/g | |
| Vitamin B12 (microbial) | | | 1.2 mcg/100 g | |
| Metal analysis by ICP/MS (trace) | Aluminum | | 129 ppm | 0.1 ppm |
| | Antimony | | <1 ppm | 0.01 ppm |
| | Arsenic | | 1 ppm | 0.01 ppm |
| | Barium | | 44.4 ppm | 0.02 ppm |
| | Beryllium | | <0.04 ppm | 0.01 ppm |
| | Bismuth | | <1 ppm | 0.02 ppm |
| Metal analysis by ICP/MS (trace) | Cadmium | | <0.1 ppm | 0.001 ppm |
| | Calcium | | 3.53 mg/g | 1.0 ppm |
| | Chromium | | 2.92 ppm | 0.02 ppm |
| | Cobalt | | <0.1 ppm | 0.01 ppm |
| | Copper | | 25.5 ppm | 0.01 ppm |
| | Iron | | 259 ppm | 0.5 ppm |
| | Lead | | <0.6 ppm | 0.01 ppm |
| | Lithium | | 2.5 ppm | 0.05 ppm |
| | Magnesium | | 10.6 mg/g | 0.02 ppm |
| | Manganese | | 7.6 ppm | 0.02 ppm |
| | Mercury | | <0.006 ppm | 0.005 ppm |
| | Molybdenum | | 2.3 ppm | 0.01 ppm |
| | Nickel | | 0.7 ppm | 0.02 ppm |

| Test | Compound | Specification Limit | Result | Detection Limit |
|---|---|---|---|---|
| | Phosphorus | | 2.66 mg/g | 1 ppm |
| | Potassium | | 4.45 mg/g | 0.5 ppm |
| | Selenium | | 0.9 ppm | 0.04 ppm |
| | Silver | | <0.4 ppm | 0.02 ppm |
| | Sodium | | 88.6 mg/g | 1 ppm |
| | Strontium | | 72.2 ppm | 0.01 ppm |
| | Thallium | | 1.3 ppm | 0.01 ppm |
| | Tin | | <0.5 ppm | 0.01 ppm |
| | Titanium | | 6.5 ppm | 0.02 ppm |
| | Vanadium | | <0.4 ppm | 0.01 ppm |
| | Zinc | | 19.7 ppm | 0.05 ppm |
| | Zirconium | | 0.4 ppm | 0.01 ppm |

Methodology:
amino acid screen (AMINO-CMPL) - USDA 6.011 (1986)
Amylase - alpha - FCC UV Spectraphotometry
Carotenoid Esters - total - UV Absorption
Chlorophyll - AOAC
Fatty Acid Profile - nutritional - P005 - Fatty Acid Profile in Food Products based on AOAC 996.06, AOCS Official Method Ce2-66
Lipase - FCC 4th edition (titration)
Metal analysis by ICP/MS (trace) - AOAC 984.27 using ICP/MS
Total Polyphenols - UV - Colorimeteric - using Folin-Ciocalteu reagent
Vitamin A - assay - H081f - Vitamin A and Beta Carotene in Food Products based on AOAC Method 970.64
Vitamin B1, B2, B3, B5, B6 package - AOAC 961.15(modified) - analysis by LC/MS/MS
Vitamin B12 (microbial) - USP 31 <171> modified for food
Vitamin C - assay - Vitamin C in Food Products based on Extraction by AOAC Methods of Analysis for Nutrition Labeling (1993) Chapter 37, Analysis by HPLC
Vitamin D assay - AOAC Method of Analysis for Nutrition Labeling (1993) Chapter 38
Vitamin E - assay - AOAC Method of Analysis for Nutrition Labeling (1993) Chapter 39, modified

Example 9

A compositional analysis of a Golden Brown Algae (6.14% Moisture Content) sample produced in accordance with the present invention is set forth.

Sample #: 62510-001
Sample Description: Golden Brown Algae, Processed at MCD Tech, 6.14% moisture content/8 mesh
Temp on Receipt: RT
Comment: ND = not detected or less than detection limit

| Test | Compound | Specification Limit | Result | Detection Limit |
|---|---|---|---|---|
| Chlorophyll | | | 570.0 mg/100 g | |
| Carotenoid Esters - total | | | 0.57% | |
| Total Polyphenols - UV | Total polyphenols | | 7.6% | n/a |
| Vitamin A - assay | Beta-carotene mcg divided by 6 | | 1172 RE/100 g | <10 IU/100 g, |
| | Retinol | | ND | <10 IU/100 g, |
| | Total vitamin A | | 1172 RE/100 g | <10 IU/100 g, |
| Vitamin C - assay | Vitamin C | | 11.4 g/100 g | 5 ppm |
| Vitamin D assay | VD2 | | ND | 10 IU/100 g |
| | VD3 | | ND | 10 IU/100 g |
| Vitamin E - assay | gamma-Tocopherol | | 108 mg/100 g | 0.1 mg/100 g |
| Vitamin Test | B1 - Thiamine | | ND | 0.1 mg/100 g |
| | B2 - Riboflavin | | 0.31 mg/100 g | 0.1 mg/100 g |
| | B3 - Niacin | | 0.51 mg/100 g | 0.1 mg/100 g |
| | B5 - Calcium D-Pantothenate | | ND | 0.1 mg/100 g |
| | B6 - Pyridoxine HCl | | ND | 0.1 mg/100 g |
| Fatty Acid Profile - nutritional | cis-Polyunsaturated fatty Acids | | 1.94% | 0.1% |
| | Omega-6 Fatty Acids | | 0.10% | 0.1% |
| | Omega-3 Fatty Acids | | 1.13% | 0.1% |
| | cis-Monounsaturated | | 0.79% | 0.1% |

-continued

Sample #: 62510-001
Sample Description: Golden Brown Algae, Processed at MCD Tech, 6.14% moisture content/8 mesh
Temp on Receipt: RT
Comment: ND = not detected or less than detection limit

| Test | Compound | Specification Limit | Result | Detection Limit |
|---|---|---|---|---|
| | Fatty Acids | | | |
| | Conjugated Fatty Acids | | <0.01% | 0.1% |
| | Saturated fatty acids | | 1.16% | 0.1% |
| | Trans fatty acids | | 0.02% | 0.01% |
| | Fat as Triglycerides | | 4.10% | 0.1% |
| amino acid screen (AMINO-CMPL) | alanine | | 1.53% | 0.10% |
| | arginine | | 1.37% | 0.10% |
| | aspartic acid | | 2.52% | 0.10% |
| | cystine | | 1.37% | 0.10% |
| | glutamic acid | | 2.67% | 0.10% |
| | glycine | | 1.37% | 0.10% |
| | histidine | | 0.48% | 0.10% |
| | hydroxyproline | | <0.01% | 0.10% |
| | isoleucine | | 1.18% | 0.10% |
| | leucine | | 2.07% | 0.10% |
| | lysine | | 1.25% | 0.10% |
| | methionine | | 0.82% | 0.10% |
| | phenylalanine | | 1.42% | 0.10% |
| | proline | | 0.33% | 0.10% |
| | serine | | 1.28% | 0.10% |
| | threonine | | 1.04% | 0.10% |
| | tryptophan | | 0.36% | 0.10% |
| | tyrosine | | 0.88% | 0.10% |
| | valine | | 1.35% | 0.10% |
| Amylase - alpha | | | <100 BAU/g | |
| Lipase | | | 158 LU/g | |
| Proteolytic activity, bacterial source | | | No Activity detected PC/g | |
| Vitamin B12 (microbial) | | | 5.5 mcg/100 g | |
| Metal analysis by ICP/MS (trace) | Aluminum | | 156 ppm | 0.1 ppm |
| | Antimony | | <1 ppm | 0.01 ppm |
| | Arsenic | | 1 ppm | 0.01 ppm |
| | Barium | | 49.5 ppm | 0.02 ppm |
| | Beryllium | | <0.04 ppm | 0.01 ppm |
| | Bismuth | | <1 ppm | 0.02 ppm |
| Metal analysis by ICP/MS (trace) | Cadmium | | <0.1 ppm | 0.001 ppm |
| | Calcium | | 4.07 mg/g | 1.0 ppm |
| | Chromium | | 2.93 ppm | 0.02 ppm |
| | Cobalt | | <0.1 ppm | 0.01 ppm |
| | Copper | | 31.3 ppm | 0.01 ppm |
| | Iron | | 321 ppm | 0.5 ppm |
| | Lead | | <0.6 ppm | 0.01 ppm |
| | Lithium | | 2.8 ppm | 0.05 ppm |
| | Magnesium | | 12.0 mg/g | 0.02 ppm |
| | Manganese | | 9.6 ppm | 0.02 ppm |
| | Mercury | | <0.006 ppm | 0.005 ppm |
| | Molybdenum | | 2.8 ppm | 0.01 ppm |
| | Nickel | | 0.6 ppm | 0.02 ppm |
| | Phosphorus | | 3.06 mg/g | 1 ppm |
| | Potassium | | 5.11 mg/g | 0.5 ppm |
| | Selenium | | 1 ppm | 0.04 ppm |
| | Silver | | <0.4 ppm | 0.02 ppm |
| | Sodium | | 104 mg/g | 1 ppm |
| | Strontium | | 82.8 ppm | 0.01 ppm |
| | Thallium | | 0.9 ppm | 0.01 ppm |
| | Tin | | <0.5 ppm | 0.01 ppm |
| | Titanium | | 8.0 ppm | 0.02 ppm |
| | Vanadium | | 0.5 ppm | 0.01 ppm |
| | Zinc | | 24.6 ppm | 0.05 ppm |
| | Zirconium | | 0.3 ppm | 0.01 ppm |

Methodology:
amino acid screen (AMINO-CMPL) - USDA 6.011 (1986)
Amylase - alpha - FCC UV Spectraphotometry
Carotenoid Esters - total - UV Absorption
Chlorophyll - AOAC
Fatty Acid Profile - nutritional - P005 - Fatty Acid Profile in Food Products based on AOAC 996.06, AOCS Official Method Ce2-66
Lipase - FCC 4th edition (titration)
Metal analysis by ICP/MS (trace) - AOAC 984.27 using ICP/MS
Total Polyphenols - UV - Colorimeteric - using Folin-Ciocalteu reagent
Vitamin A - assay - H081f - Vitamin A and Beta Carotene in Food Products based on AOAC Method 970.64

Sample #: 62510-001
Sample Description: Golden Brown Algae, Processed at MCD Tech, 6.14% moisture content/8 mesh
Temp on Receipt: RT
Comment: ND = not detected or less than detection limit

| Test | Compound | Specification Limit | Result | Detection Limit |
|------|----------|---------------------|--------|-----------------|

Vitamin B1, B2, B3, B5, B6 package - AOAC 961.15(modified) - analysis by LC/MS/MS
Vitamin B12 (microbial) - USP 31 <171> modified for food
Vitamin C - assay - Vitamin C in Food Products based on Extraction by AOAC Methods of Analysis for Nutrition Labeling (1993) Chapter 37, Analysis by HPLC
Vitamin D assay - AOAC Method of Analysis for Nutrition Labeling (1993) Chapter 38
Vitamin E - assay - AOAC Method of Analysis for Nutrition Labeling (1993) Chapter 39, modified

Comparative Analysis of Fatty Acid Content Present within Various Samples Produced by the Presently Disclosed Invention

Example 10

A comparative analysis showing the fatty acid profiles of various phytoplankton specimens produced in accordance with the present invention is set forth.
Algae from Vancouver, BC.

| Drying method | Fatty acid profiles (%)* | | | | | | | | | | | |
|---|---|---|---|---|---|---|---|---|---|---|---|---|
| | 14:0 | 16:0 | 16:1 | 16:2 | 16:4 | 18:0 | 18:3 | 18:4 | 20:1 | 20:2 | 22:0 | 22:6 |
| Freeze drying | 5.3 | 4.3 | 9.8 | 13 | 8.6 | 14.7 | 19.4 | 2.1 | 2 | 1.7 | 15.6 | 1.5 |
| Spray drying | 5.8 | 5.6 | 10.6 | 3.9 | 10.5 | 18.2 | 13 | 2.6 | 2.5 | 0.9 | 20.2 | 2.1 |
| Refractance Window drying | 5.2 | 4 | 9.1 | 14.2 | 9 | 15.6 | 14.9 | 2.1 | 2.4 | 3.2 | 15.1 | 1.6 |

Green Algae from Arizona

| Drying method | Fatty acid profiles (%)* | | | | | | | | |
|---|---|---|---|---|---|---|---|---|---|
| | 14:0 | 16:0 | 16:1 | 18:0 | 18:1 | 18:2 | 18:3 | 20:4 | 22:0 |
| Freeze drying | 3.5 | 39.4 | 22.1 | 1.4 | 4.2 | 1.7 | 1.2 | 2.7 | 14.0 |
| Spray drying | 3.6 | 42. | 20.2 | 1.5 | 4.4 | 1.5 | 2.3 | 2.8 | 14.0 |
| Refractance Window drying | 3.6 | 37.8 | 18.4 | 1.2 | 4.3 | 1.7 | 4.5 | 3.4 | 17.2 |

*Note: numbers may not add up to 100% because of other minor peaks in chromatogram that could be classified with certainty. Highlighted areas denote the polyunstaturated fatty acids (PUFA) of interest.

| Arizona algae | Vancouver algae |
|---|---|
| 18:2 Linoleic acid (Omega-6 fatty acid) | 16:4 Hexadecatetraenoic acid |
| 18:3 Linolenic acid (Omega-3 fatty acid) | 18:3 Linolenic acid (Omega-3) |
| | 18:4 Stearidonic acid (a UFA) |
| 20:4 Arachidonic acid (Omega-6 fatty acid) | 22:6 Docosahexaeniic acid (Omega-3) |

BRIEF SUMMARY

Longer chain fatty acids, including the 22:6 omega-3 fatty acid was detected in algae from Vancouver than in the Arizon material, while arachidonic acid (20:4—omega-6), a polyunsaturated fatty acid (PUFA) was detected in Arizona algae. Fatty acid profile for Vancouver algae appears wide, from the completely saturated 14:0 to the 22:6 PUFA. Algae from the two locations contain sizable amounts of docosanoate (22:0). These materials were neither purified nor extracted with specific objective of enhancing the concentration of PUFA's. Freeze drying and Refractance Window drying showed comparable effect on fatty acids. At this stage a defininte conclusion on amlunts of fatty acids retained by the three drying methods cannot be made.

Although the foregoing invention has been described in detail by way of illustration and example for purposes of clarity and understanding, it will be appreciated and obvious to those people skilled in the art that certain changes and modifications may be practiced without departing from the spirit and scope thereof, as described in this specification.

What is claimed is:

1. A method of growing and harvesting multiple species of phytoplankton, comprising the steps of:
    collecting phytoplankton seawater containing multiple species of naturally-occurring phytoplankton directly from a source of seawater;
    substantially depriving the collected phytoplankton seawater of light for about 48 consecutive hours before adding nutrients;
    adding nutrients to the light deprived phytoplankton seawater to proliferate the multiple species of naturally-occurring phytoplankton to a predetermined density, wherein the growth cycle of the phytoplankton deprived of light for about 48 consecutive hours is faster than the growth cycle for non-light deprived phytoplankton;
    separating the multiple species of naturally-occurring phytoplankton from the phytoplankton seawater to form a phytoplankton concentrate; and collecting the phytoplankton concentrate, wherein the phytoplankton of the phytoplankton concentrate remain in a substantially intact cellular state.

2. The method of claim 1, wherein the phytoplankton seawater is filtered prior to substantially depriving the collected phytoplankton seawater of light so as to remove organic and inorganic materials having a size greater than about four millimeters.

3. The method of claim 1, wherein the collected phytoplankton seawater is stored in a storage facility, wherein the storage facility includes at least one storage tank.

4. The method of claim 3, wherein the at least one storage tank has a volumetric capacity of about 1,000,000 liters.

5. The method of claim 1, wherein the collected phytoplankton is aerated with an oxygen-containing gas.

6. The method of claim 3, wherein the collected phytoplankton seawater is maintained in the at least one storage tank for a time ranging from about 48 hours to about 7 days.

7. The method of claim 1, wherein the nutrients include one or more of phosphorous, soluble potash, boron, chelated copper, chelated iron, chelated manganese, molybdenum, chelated zinc, ethylemediamine, organic soluble fillers, fish waste, human waste, and animal waste.

8. The method of claim 1, wherein the multiple species of phytoplankton proliferate in at least one tank having a volumetric capacity of about 1,000,000 liters.

9. The method of claim 1, wherein a volume of seawater is added to the multiple species of phytoplankton during proliferation.

10. The method of claim 9, wherein the volume of seawater is about 750,000 liters.

11. The method of claim 1, wherein at least one monitoring measurement of the phytoplankton seawater is periodically taken during proliferation, the at least one monitoring measurement including temperature of the phytoplankton seawater, turbidity of the phytoplankton seawater, pH of the phytoplankton seawater, dissolved oxygen concentration of the phytoplankton seawater, ammonia concentrations of the phytoplankton seawater, phosphate concentrations of the phytoplankton seawater, and weather conditions.

12. The method of claim 1, wherein the predetermined density is about 500,000 cells of multiple species of naturally-occurring phytoplankton per milliliter of phytoplankton seawater.

13. The method of claim 1, wherein the multiple species of phytoplankton are proliferated at a temperature ranging from about −10 to about 30 degree Celsius.

14. The method of claim 1, wherein the multiple species of phytoplankton are separated from the phytoplankton seawater by at least one filter, thereby forming a filtered seawater effluent.

15. The method of claim 14, wherein the filtered seawater effluent is recycled directly to the source of the seawater.

16. The method of claim 1, wherein the multiple species of phytoplankton are concentrated by gravitational settling.

17. The method of claim 16, wherein the multiple species of phytoplankton are further concentrated by electrical current.

18. The method of claim 1, wherein the multiple species of phytoplankton are both separated and concentrated by electrical current.

19. The method of claim 1, wherein the concentrated phytoplankton is a powder or a liquid.

20. A method of growing and harvesting multiple species of phytoplankton, comprising the steps of:

transporting a first volume of phytoplankton seawater containing multiple species of naturally-occurring phytoplankton directly from a source of seawater to at least one tank;

substantially depriving the first volume of phytoplankton seawater of light in the tank for about 48 consecutive hours before adding nutrients;

adding nutrients to the light deprived phytoplankton seawater contained in the tank to proliferate the multiple species of naturally-occurring phytoplankton to a predetermined density, wherein the growth cycle of the phytoplankton deprived of light for about 48 consecutive hours is faster than the growth cycle for non-light deprived phytoplankton;

withdrawing a volume of the phytoplankton seawater from the tank while simultaneously adding a second volume of seawater containing multiple species of naturally-occurring phytoplankton directly from the source of seawater to the tank, such that the second volume of seawater added is substantially equivalent to the volume of phytoplankton seawater withdrawn from the tank thereby maintaining a continuous and constant volume of seawater containing multiple species of naturally-occurring phytoplankton in the tank;

separating the multiple species of naturally-occurring phytoplankton from the withdrawn phytoplankton seawater to form a phytoplankton concentrate; and collecting the phytoplankton concentrate.

21. The method of claim 20, wherein the first volume of phytoplankton seawater is filtered prior to adding the nutrients so as to remove organic and inorganic material having a size greater than about four millimeters.

22. The method of claim 20, wherein the tank has a volumetric capacity of about 1,000,000 liters.

23. The method of claim 20, wherein the first volume of phytoplankton seawater is aerated with an oxygen-containing gas.

24. The method of claim 20, wherein the first volume of phytoplankton seawater is maintained in the tank for a time ranging from about 48 hours to about 7 days.

25. The method of claim 20, wherein the nutrients include one or more of phosphorous, soluble potash, boron, chelated copper, chelated iron, chelated manganese, molybdenum, chelated zinc, ethylenediamine, organic soluble fillers, fish waste, human waste, and animal waste.

26. The method of claim 20, wherein at least one monitoring measurement of the phytoplankton seawater is periodically taken during proliferation, the at least one monitoring measurement including temperature of the phytoplankton seawater, turbidity of the phytoplankton seawater, pH of the phytoplankton seawater, dissolved oxygen concentration of the phytoplankton seawater, ammonia concentrations of the phytoplankton seawater, phosphate concentrations of the phytoplankton seawater, and weather conditions.

27. The method of claim 20, wherein the predetermined density is about 500,000 cells of multiple species of naturally-occurring phytoplankton per milliliter of phytoplankton seawater.

28. The method of claim 20, wherein the multiple species of phytoplankton are proliferated at a temperature ranging from about −10 to about 30 degrees Celsius.

29. The method of claim 20, wherein the second volume of seawater containing multiple species of phytoplankton is filtered prior to being added to the tank so as to remove organic and inorganic material having a size greater than about four millimeters.

30. The method of claim 20, wherein the constant volume of seawater containing multiple species of phytoplankton is about 1,000,000 liters.

31. The method of claim 20, wherein the multiple species of phytoplankton are separated from the phytoplankton seawater by at least one filter, thereby forming a filtered seawater effluent.

32. The method of claim 31, wherein the filtered seawater effluent is recycled directly to the source of seawater.

33. The method of claim 31, wherein the filter is a rotary drum filter.

* * * * *

UNITED STATES PATENT AND TRADEMARK OFFICE
CERTIFICATE OF CORRECTION

PATENT NO. : 9,090,881 B2  
APPLICATION NO. : 12/603239  
DATED : July 28, 2015  
INVENTOR(S) : Margaret Harper and Arturo Ramirez Page 1 of 1

It is certified that error appears in the above-identified patent and that said Letters Patent is hereby corrected as shown below:

In the Specification:  
Column 3, line 54: Delete "ethylemediamine;" and insert -- ethylenediamine; --

In the Claims:  
Column 33, line 23, Claim 7: Delete "ethylemediamine," and insert -- ethylenediamine, --

Signed and Sealed this  
First Day of December, 2015

Michelle K. Lee  
*Director of the United States Patent and Trademark Office*